United States Patent
Shine et al.

(10) Patent No.: US 6,668,229 B1
(45) Date of Patent: *Dec. 23, 2003

(54) METHOD FOR TESTING A CELL SAMPLE

(76) Inventors: Thomas Adam Shine, 220 Lawrence St., No. 3, Newhaven, CT (US) 06511; Ian Basil Shine, 444 Central Park West, New York, NY (US) 10025

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 131 days.

(21) Appl. No.: 09/101,005
(22) PCT Filed: Dec. 27, 1996
(86) PCT No.: PCT/GB96/03256
§ 371 (c)(1), (2), (4) Date: Aug. 4, 1998
(87) PCT Pub. No.: WO97/24598
PCT Pub. Date: Jul. 10, 1997

(30) Foreign Application Priority Data

Dec. 29, 1995 (GB) .............................. 9526684

(51) Int. Cl.$^7$ ......................... G01N 15/00; G01N 15/10
(52) U.S. Cl. ............................. 702/21; 435/2
(58) Field of Search .................. 435/2, 372; 702/21; 324/7.4; 436/63, 68

(56) References Cited

U.S. PATENT DOCUMENTS

| | | | |
|---|---|---|---|
| 3,502,412 A | 3/1970 | Burns | 356/40 |
| 3,851,246 A | * 11/1974 | Curby et al. | 324/71 |
| 4,081,340 A | 3/1978 | Zimmermann | 435/173.5 |
| 4,240,027 A | 12/1980 | Larsen | 324/638 |
| 4,271,001 A | 6/1981 | Imafuku | 204/406 |
| 4,278,936 A | 7/1981 | Shine | 324/17 CP |
| 4,298,836 A | 11/1981 | Groves et al. | 324/71 CP |
| 4,374,644 A | * 2/1983 | Armstrong | 436/63 |
| 4,521,729 A | 6/1985 | Kiesewetter et al. | 324/71.1 |
| 4,525,666 A | 6/1985 | Groves | 324/71.1 |
| 4,535,284 A | * 8/1985 | Groves et al. | 324/71.1 |
| 4,791,355 A | 12/1988 | Coulter et al. | 324/71.1 |
| 4,810,963 A | 3/1989 | Blake-Coleman et al. | 324/204 |
| 4,876,504 A | 10/1989 | Blake et al. | 324/204 |
| 5,006,460 A | 4/1991 | Thomas, Jr. et al. | 435/6 |
| 5,464,752 A | 11/1995 | Kortright et al. | 435/7.24 |
| 5,532,139 A | 7/1996 | Miller | 435/29 |
| 5,700,632 A | * 12/1997 | Critser et al. | 435/2 |
| 5,856,665 A | 1/1999 | Price et al. | 250/205 |

FOREIGN PATENT DOCUMENTS

| | | | |
|---|---|---|---|
| CA | 988319 | 4/1980 | |
| EP | 0 010 526 | 4/1980 | |
| EP | 0 595 352 | 5/1994 | G01N/33/487 |

OTHER PUBLICATIONS

Linderkamp et al. Geometric, osmotic, and membrane mechanical properties of density–seperated human red cell. Blood 59 (6), pp. 1121–1127. (Jun. 1992).*

Eskelinen et al. Cation permeability and mechanical properties of the erythrocyte membrane under the influence of lysophosphatidylcholine (LPC) in isotonic and hypotonic media. Acta Physiol. Scand. 122 (4), pp. 527–534. (Dec. 1984).*

Richieri et al. Measurement of biophysical properties of red blood cells by resistive pulse spectroscopy: volume, shape, surface area, and deformability. J. Biochem. And Biophys. Methods 11, pp. 117–131. (1985). No month found.*

A Method for Production of N2 Microbubbles in Platelet–Rich Plasma in an Aggregometer–like Apparatus, and Effect on the Platelet Density in Vitro Undersea Biomedical Research (Thorsen et al.), vol. 13, No. 3; Sep. 1986; pp. 271–288.

Spreading of Cells on Various Substrates Evaluated by Fourier Analysis of Shape Histochemistry (Kieler et al.); 1989; vol. 92; pp. 141–148.

* cited by examiner

Primary Examiner—Marjorie Moran

(57) ABSTRACT

In this invention, a measurement of cell permeability is determined by obtaining a measure of the volume of fluid which crosses a sample cell membrane in response to an altered environment. A lytic agent may be used to drive fluid across the cell membranes and thereby cause a change in cell volume. An alteration in osmolality of a sample suspension is preferred, in which the sample suspension is subjected to a continuous osmotic gradient.

19 Claims, 15 Drawing Sheets

Fig. 10C.

| N=5 | Time | Cp | IsoU | Ypk | pko | Real C | Diam | S.I. | Dipth | RBC |
|---|---|---|---|---|---|---|---|---|---|---|
| Mean | --- | 4.25 | 82.52 | 151.57 | 132.18 | 4987.8 | 6.62 | 14.98 | 1.05 | 2114.9 |
| S.D. | --- | 0.03 | 0.26 | 0.32 | 0.85 | 106.77 | 0.00 | 0.06 | 0.01 | 46.46 |
| S.E | --- | 0.01 | 0.12 | 0.14 | 0.38 | 47.75 | 0.00 | 0.03 | 0.00 | 20.78 |
| CU | --- | 0.73 | 0.31 | 0.21 | 0.65 | 2.14 | 0.07 | 0.41 | 0.60 | 2.20 |
| 5 | 3:12:57 PM | 4.26 | 82.87 | 151.24 | 130.93 | 5095.2 | 6.61 | 14.90 | 1.06 | 2137.8 |
| 4 | 3:11:32 PM | 4.24 | 82.51 | 151.82 | 132.95 | 5077.0 | 6.62 | 15.00 | 1.05 | 2166.5 |
| 3 | 3:10:06 PM | 4.21 | 82.65 | 151.37 | 132.96 | 5009.8 | 6.61 | 14.94 | 1.05 | 2138.0 |
| 2 | 3:08:49 PM | 4.27 | 82.35 | 151.46 | 131.80 | 4907.2 | 6.61 | 14.99 | 1.06 | 2074.1 |
| 1 | 3:06:13 PM | 4.29 | 82.21 | 151.99 | 132.28 | 4849.5 | 6.62 | 15.06 | 1.05 | 2058.0 |

Summary Statistics

Fig.14.
| RESULTS | Value | Units | μ±4SD | Date |
|---|---|---|---|---|
| Sphering pressure | 85.02 | mOsm/Kg | 143.70 | 6/4/93 |
| Cp net | 3.48 | ml/m^2 | 3.10 | 6/4/93 |
| S.I. | 14.5 | -- | 17.50 | 6/4/93 |
| IsoV | 66.42 | fl | 91.00 | 6/4/93 |
| SphV | 96.46 | fl | 160.00 | 6/4/93 |
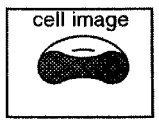
cell image
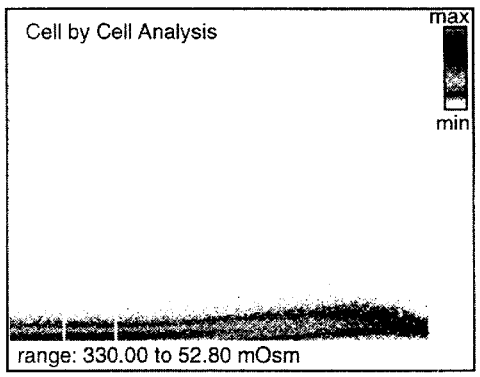
Cell by Cell Analysis
max / min
range: 330.00 to 52.80 mOsm
Frequency Distributions
| Dist. | mean | SD | cv | skew | kurt | n |
|---|---|---|---|---|---|---|
| Isotonic | 16.45 | 7.02 | 43 | 4.0 | 39.9 | 43121 |
| Spherical | 24.39 | 9.76 | 40 | 1.0 | 1.9 | 2598 |
| Ghost | 19.54 | 6.96 | 36 | 1.1 | 1.5 | 1276 |
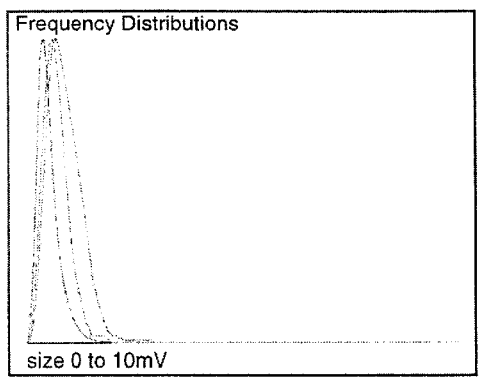
Frequency Distributions
size 0 to 10mV

METHOD FOR TESTING A CELL SAMPLE

This application is a §371 application of PCT/GB96/03256, filed Dec. 27, 1996.

TECHNICAL FIELD

The present invention relates to a method of measuring cell membrane permeability and is applicable to all types of cells, including red cells, white cells, platelets, fibroblasts, tissue cells, amoebae, fungi, bacteria, all eucaryotic and procaryotic cells as well as synthesized cells or particles.

BACKGROUND ART

Permeability is the passage of matter in a fluid or gaseous state through another material, usually in a solid state, measured as a rate or total volume transferred across a membrane per unit time per unit surface area at standard temperature and pressure. Biologically, many membranes, especially cell membranes, are selectively permeable enabling cells to transfer nutrients, hormones, gases, sugars, proteins or water across their membranes. This transport may be passive, depending solely upon the partial pressures or concentrations of the substances on either side of the membrane or it may be active, requiring energy to counter existing concentrations. Different cells have different molecule specific rates of permeability which are closely related to the cell's function.

Current tests of red cell permeability produce a single value for permeability, typically by measuring the change in concentration of a radio labelled molecule (often water) in or around a cell (or a population of cells).

DISCLOSURE OF INVENTION

According to the present invention there is provided a new method in which a sample of cells suspended in a liquid medium, wherein the cells have at least one measurable property distinct from that of the liquid medium, is subjected to analysis to determine a measure of cell permeability of the sample of cells by a method including the steps:

(a) passing a first aliquot of the sample cell suspension through a sensor, (b) measuring said at least one property of the cell suspension, (c) recording the measurement of said property for the first aliquot of cells, (d) subjecting a second aliquot of the sample cell suspension to an alteration in at least one parameter of the cell environment which has the potential to induce a flow of fluid across the cell membranes and thereby alter the said at least one property of the cells, (e) passing said second aliquot through a sensor, (f) measuring said at least one property of the cell suspension under the altered environment, (g) recording the measurement of said at least one property for the second aliquot of cells, (h) comparing the data from steps (c) and (g) as a function of the extent of said alteration of said parameter of the cell environment and change in the recorded measurements of said at least one property to determine a measure of cell permeability of the sample.

Blood cells travel through the entire body once a minute continually transporting gases and metabolites. Blood cells also act as messengers or surrogate hormones, transmitting information around the body. It has been discovered that this peripatetic existence allows the blood cells to signal distant pathology. For example, when the brain dies, when a limb has an occluded blood supply or the kidney fails to remove essential toxins, the blood cell's membrane permeability changes. Cell membrane permeability has never been measured routinely and only rarely measured experimentally. Until now, there have been no rapid or reliable methods of performing such measurements. It has also been discovered that red cell permeability is complex, dynamically changing as molecules cross the cell's membrane depending on, for example, the shape and structure of the cell and membrane pump activity. The method of the present invention produces existing measures of permeability, but more usefully it produces more sensitive, accurate and descriptive measures of cell permeability within sixty seconds with no sample preparation.

Preferably, the property of the cells which differs from the liquid medium is one which is directly related to the volume of the cell. Such a property is electrical resistance or impedance which may be measured using conventional particle counters such as the commercially available instrument sold under the trade name Coulter Counter by Coulter Instruments Inc. Preferably, the sensor used to detect cells and measure a change in the cells' property is that described in our co-pending International application (Agent's reference 62/2681/03). In this apparatus the cell suspension is caused to flow through an aperture where it distorts an electrical field. The response of the electrical field to the passage of the cells is recorded as a series of voltage pulses, the amplitude of each pulse being proportional to cell size.

In the preferred method of the present invention, a measurement of cell permeability is determined by obtaining a measure of the volume of fluid which crosses a sample cell membrane in response to an altered environment. The environmental parameter which is changed in the method may be any change which results in a measurable property of the cells being altered. Preferably, a lytic agent is used to drive fluid across the cell membranes and thereby cause a change in cell volume. Preferably therefore, the environmental parameter change is an alteration in osmolality, most preferably a reduction in osmolality. Typically, the environment of the first aliquot is isotonic and thus the environment of the second aliquot is rendered hypotonic. Other suitable lytic agents include soap, alcohols, poisons, salts, and an applied shear stress.

It is possible to subject only a single aliguot of sample suspension to one or more alterations in osmolality to achieve this effect, although is preferred to use two or more different aliquots of the same sample suspension. Most preferably, the sample suspension is subjected to a continuous osmotic gradient, and in particular an osmotic gradient generated in accordance with the method of our co-pending International application (Agent's reference 80/4936/03).

In the preferred method of our co-pending International application (Agent's reference 62/2734/03), a number of measurements of particular cell parameters are made over a continuous series of osmolalities, including cell volume and cell surface area, which takes account of the deviation of the cells from spherical shape particles commonly used to calibrate the instruments. An estimate of in vivo cell shape made so that an accurate measurement of cell volume and cell surface area at all shapes is obtained. A sample suspension is fed continuously into a solution the osmolality of which is changed continuously to produce a continuous concentration gradient. Reducing the osmolality of the solution surrounding a red blood cell below a critical level causes the cell first to swell, then rupture, forming a ghost cell which slowly releases its contents, almost entirely haemoglobin, into the surrounding medium. The surface area of the each cell remains virtually unchanged on an increase in cell volume due to a reduction in osmolality of the cell's environment as the cell membrane is substantially inelastic. The time between initiation of the alteration of the environment in each aliquot to the passage of the cells through the sensing zone is kept constant so that time is not a factor in any calculation in cell permeability. An effect of feeding the sample under test into a continuously changing osmolality gradient, is to obtain measurements which are equivalent to treating one particular cell sample with that continuously changing gradient.

Preferably, the measurements are recorded on a cell-by-cell basis in accordance with the method of our co-pending International application (Agent's reference 62/2734/03). The number of blood cells within each aliquot which are counted is typically at least 1000 and the cell-by-cell data is then used to produce an exact frequency distribution of cell permeability. Suitably this density can be displayed more visibly by using different colours to give a three dimensional effect, similar to that seen in radar rainfall pictures used in weather forecasting. Alternatively, for a single solution of any tonicity, the measured parameter change could be displayed against a number of individual cells showing the same change. In this way a distribution of cell permeability in a tonicity of given osmolality can be obtained.

As discussed above, the methods in our co-pending applications can provide an accurate estimate of cell volume, or other cell parameter related to cell volume, and cell surface area over a continuous osmotic gradient for individual cells in a sample. A plot of change in cell volume against osmolality reveals a characteristic curve showing how the cell volume changes with decreasing osmolality and indicates maximum and minimum rates of flow across the membrane and the flow rates attributed to a particular or series of osmotic pressures.

Having obtained measures of osmotic pressure ($P_{osm}$) cell volume, surface area (SA) and other relevant environmental factors, it is possible to obtain a number of measures of cell permeability:

1) Cp rate

This coefficient of permeability measures the rate of fluid flow across a square meter of membrane in response to a specified pressure. All positive rates represent a net flow into the cell, while all negative rates are the equivalent of a net flow out of the cell. The rate is determined by:

$Cp$ rate=$\Delta$cell volume/$\Delta P_{osm}$/SA at S.T.P.

2) Permeability Constant $pk_n$

This set of permeability measures describe each pressure where the net permeability rate is zero, and are numbered $pk_0$, $pk_1$ ... $pk_n$.
  (i) $pk_0$ coincides with the minimum absolute pressure (hypotonic) to which a cell can be subjected without loss of integrity. A pressure change of one tenth of a milliosmole per kg (0.0001 atms) at $pk_0$ produces a change in permeability of between one and two orders of magnitude making $pk_0$ a distinct, highly reproducible measure.
  (ii) $pk_1$ is a measure of the cells' ability to volumetrically regulate in slightly hypotonic pressures. After a certain pressure, the cell can no longer defeat the osmotic force, resulting in a change in the cell's volume. $pk_1$ provides a measure of the cells ability to perform this regulation, thereby measuring a cell's maximum pump transfer capability.
  (iii) $pk_2$, a corollary of $pk_1$, is a measure of the cells ability to volumetrically regulate in hypertonic pressures, and occurs at low differential pressures, when compared to the cell's typical in vivo hydrostatic pressure.

The permeability constant $pk_n$ is described by the following equation:

$pk_n=\Delta P_{osm}$/SA at S.T.P.

When calculating $pk_0$, $\Delta P_{osm}$=(isotonic pressure)–(pressure where net flow is zero).

When calculating $pk_1$, $\Delta P_{osm}$=(isotonic pressure)–(first hypotonic pressure where net positive flow begins). The calculation of $pk_2$ is identical to $pk_1$, except $\Delta P_{osm}$ measures the first hypertonic pressure where net positive flow is not zero.

3) CPΔ

This dimensionless value is the comparison of any two Cp rates, and is expressed as the net amount of fluid to cross the cell membrane between any two lytic concentrations. It provides a volume independent and pressure dependent comparison of permeability rates. This measure may be used to compare permeability changes in the same individual over a period ranging from minutes to months.

4) $Cp_{max}$

This is the maximum rate of flow across the cell's membrane. For almost all cells, there are two maxima, one positive (net flow into the cell) and one negative (net flow out of the cell) situated either side of $ph_0$. $Cp_{max}$ is determined by detecting the maximum positive and negative gradients of the continuous curve of change in cell volume against osmolality.

5) Membrane Structural Resistance (MSR)

This is a measure of the structural forces inside a cell which resist the in-flow or out-flow of water. It is determined by the ratio of $Cp_{max}$ to all other non-zero flow rates into the cell. As the membrane is theoretically equally permeable at all pressures, change from the maximum flow rate outside the pressure range of $pk_1$ to $pk_2$ are due to mechanical forces. It is clear that $pk_0$ is an entirely mechanical limit on the cell because as $Cp_{rate}$ approaches zero, MSR approaches ∞, thereby producing more strain than the membrane can tolerate.

$MSR=Cp_{max}/Cp_{rate} \times 100\%$ 6) cpml

This is a measure of the physiological permeability available to an individual per unit volume of tissue or blood, or for the whole organ or total body, and is calculated by:

$CP$ ml=$\Delta$cell volume/$\Delta P_{osm}$/m$^3$ per ml of whole blood.

The method of the present invention has a wide range of uses, in particular:
1. A means of measuring permeability and permeability rates on any type of cell.
2. A means for detecting and differentiating normal and abnormal membrane permeabilities and their causes.
3. An in vitro substitute for in vivo animal tests or human experimentation on new drugs, or toxicology experiments, and in particular the effect from unknown substances upon membrane permeability, such as nerve agents, anaesthetics, drugs, radiation and chemical warfare agents.

4. Membrane research.
5. Taxonomy. Different species have different membrane permeabilities which has been known but never used as a basis for taxonomy.
6. A model for other cells, particularly nerve cells, which are dependent upon membrane pumps for nerve impulse propagation.
7. In medicine for blood banking. Currently donated blood units have their shelf life limited to three weeks because some donated blood units do not survive in storage longer than this. However, the majority of units are viable for many more weeks but hospitals do not risk using a non-viable unit for transfusion. The permeability measurements of the present invention provide a means of determining the viability of blood, enabling a quick and cheap method of determining if a unit has expired. It can also be used as a basis for deciding when to discard a unit before the three week limit, thereby reducing the risk of a bad transfusion and potentially saving millions of units each year.
8. As a means for the detection of disease, diagnosis of disease, confirmation of diagnosis, monitoring prognosis of disease, monitoring treatment efficacy and monitoring remission in humans and all other species.
9. As a means of investigating pathophysiology in all species. There are many diseases that have been found to have altered cell membrane permeability that were previously unknown. For example it is altered when insulin binding to the red cell is increased as in anorexia nervosa, when anoxia induced by respiratory failure or congenital diaphragmatic hernia, or in thalassaemia intermedia, due to an undetermined mechanism. Hitherto cell permeability has never been used to monitor blood flow to a limb. One new and unexpected discovery is that occlusion of the blood flow to the lower limb sufficient to require femoral artery bypass, invariably and profoundly changes the red cell membrane permeability.
10. As a means for detecting and confirming death. At death, there is an alteration of cell membrane permeability that is quicker and cheaper to measure than an EEC.
11. Screening of routine samples for abnormality as an indication of disease.

BRIEF DESCRIPTION OF DRAWINGS

The present invention will now be described in detail with reference to the accompanying drawings, in which:

FIGS. 10*a* to 10*d* show the results from the test of a healthy individual;

FIG. 14 shows a three-dimensional frequency distribution plot and cell parameters for an abnormal individual.

DETAILED DESCRIPTION

Figure 1:
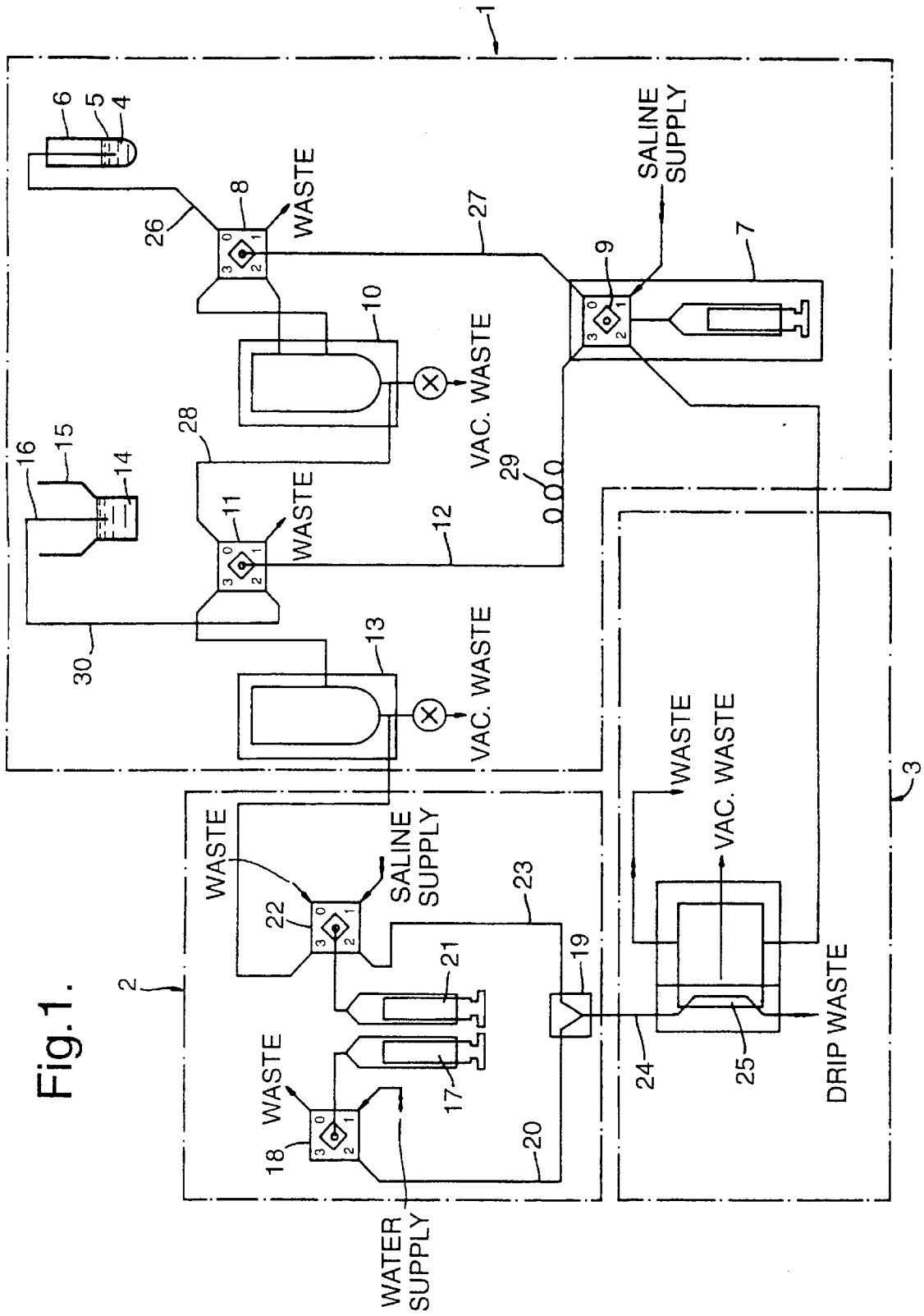
FIG. 1 shows schematically an instrument used to sample and test blood cells.

FIG. 1 shows schematically the arrangement of a blood sampler for use in the method of the present invention. The blood sampler comprises a sample preparation section 1, a gradient generator section 2 and a sensor section 3.

A whole blood sample 4 contained in a sample container 5 acts as a sample reservoir for a sample probe 6. The sample probe 6 is connected along PTFE fluid line 26 to a diluter pump 7 via multi-position distribution valve 8 and multi-position distribution valve 9. The diluter pump 7 draws saline solution from a reservoir (not shown) via port #1 of the multi-position distribution valve 9. As will be explained in detail below, the diluter pump 7 is controlled to discharge a sample of blood together with a volume of saline into a first well 10 as part of a first dilution step in the sampling process.

In a second dilution step, the diluter pump 7 draws a dilute sample of blood from the first well 10 via multi-position distribution valve 11 into PTFE fluid line 12 and discharges this sample together with an additional volume of saline into a second well 13. The second well 13 provides the dilute sample source for the gradient generator section 2 described in detail below.

Instead of using whole blood, a pre-diluted sample of blood 14 in a sample container 15 may be used. In this case, a sample probe 16 is connected along PTFE fluid line 30, multi-position distribution valve 11, PTFE fluid line 12 and multi-position distribution value 9 to the diluter pump 7. In a second dilution step, the diluter pump 7 draws a volume of the pre-diluted sample 14 from the sample container 15 via fluid line 30 and multi-position distribution value 11 into fluid line 12 and discharges the sample together with an additional volume of saline into the second well 13 to provide the dilute sample source for the gradient generator section 2.

The gradient generator section 2 comprises a first fluid delivery syringe 17 which draws water from a supply via multi-position distribution valve 18 and discharges water to a mixing chamber 19 along PTFE fluid line 20. The gradient generator section 2 also comprises a second fluid delivery syringe 21 which draws the diluted sample of blood from the second well 13 in the sample preparation section 1 via multi-position distribution valve 22 and discharges this to the mixing chamber 19 along PTFE fluid line 23 where it is mixed with the water from the first fluid delivery syringe 17. As will be explained in detail below, the rate of discharge of water from the first fluid delivery syringe 17 and the rate of discharge of dilute blood sample from the second fluid delivery syringe 21 to the mixing chamber is controlled to produce a predetermined concentration profile of the sample suspension which exits the mixing chamber 19 along PTFE fluid line 24. Fluid line 24 is typically up to 3 metres long.

A suitable gradient generator is described in detail in the Applicant's co-pending International application also filed this day (Agent's reference 62/2684/03).

As will also be explained in detail below, the sample suspension exits the mixing chamber 19 along fluid line 24 and enters the sensor section 3 where it passes a sensing zone 25 which detects individual cells of the sample suspension before the sample is disposed of via a number of waste outlets.

In a routine test, the entire system is first flushed and primed with saline, as appropriate, to clean the instrument, remove pockets of air and debris, and reduce carry-over.

The diluter pump 7 comprises a fluid delivery syringe driven by a stepper motor (not shown) and is typically arranged initially to draw 5 to 10 ml of saline from a saline reservoir (not shown) via port #1 of multi-position distribution valve 9 into the syringe body. A suitable fluid delivery syringe and stepper motor arrangement is described in detail in the Applicant's co-pending International application also filed this day (Agents reference 80/4936/03). Port #1 of the multi-position distribution valve 9 is then closed and port #0 of both multi-position distribution valve 9 and multi-position distribution valve 8 are opened. Typically 100 $\mu$l of whole blood is then drawn from the sample container 5 to take up the dead space in the fluid line 26. Port #0 of multi-position distribution valve 8 is then closed and any blood from the whole blood sample 4 which has been drawn into a fluid line 27 is discharged by the diluter pump 7 to waste via port #1 of multi-position distribution valve 8.

In a first dilution step, port #0 of multi-position distribution value 8 is opened and the diluter pump 7 draws a known volume of whole blood, typically 1 to 20 $\mu$l, into PTFE fluid line 27. Port #0 is then closed, port #2 opened and the diluter pump 7 discharges the blood sample in fluid line 27 together with a known volume of saline in fluid line 27, typically 0.1 to 2 ml, into the first well 10. Port #2 of multi-position distribution value 8 and port #0 of multi-position distribution value 9 are then closed.

Following this, port #0 of multi-position distribution valve 11 and port #3 of multi-position distribution valve 9 are opened to allow the diluter pump 7 to draw the first sample dilution held in the first well 10 to take up the dead space in PTFE fluid line 28. Port #0 of multi-position distribution valve 11 is then closed and port #1 opened to allow the diluter pump 7 to discharge any of the first sample dilution which has been drawn into fluid line 12 to waste via port #1.

In a second dilution step, port #0 of multi-position distribution valve 11 is re-opened and the diluter pump 7 draws a known volume, typically 1 to 20 $\mu$l, of the first sample dilution into fluid line 12. Fluid line 12 includes a delay coil 29 which provides a reservoir to prevent the sample contaminating the diluter pump 7. Port #0 of multi-position distribution valve 11 is then closed, port #3 opened, and the diluter pump 7 then discharges the first sample dilution in fluid line 12, together with a known volume of saline, typically 0.1 to 20 ml, into the second well 13. Port #3 of multi-position distribution valve 11 is then closed. At this stage, the whole blood sample has been diluted by a ratio of typically 10000:1. As will be explained below, the instrument is arranged automatically to control the second dilution step to vary the dilution of the sample suspension to achieve a predetermined cell count to within a predetermined tolerance at the start of a test routine.

In the gradient generator section 2, the first fluid delivery syringe 17 is primed with water from a water reservoir. Port #3 of multi-position distribution valve 22 is opened and the second fluid delivery syringe draws a volume of the dilute blood sample from the second well 13 into the syringe body. Port #3 of multi-position distribution valve 22 is then closed and port #2 of both multi-position distribution valve 18 and multi-position distribution valve 22 are opened prior to the controlled discharge of water and dilute blood sample simultaneously into the mixing chamber 19.

Figure 2:
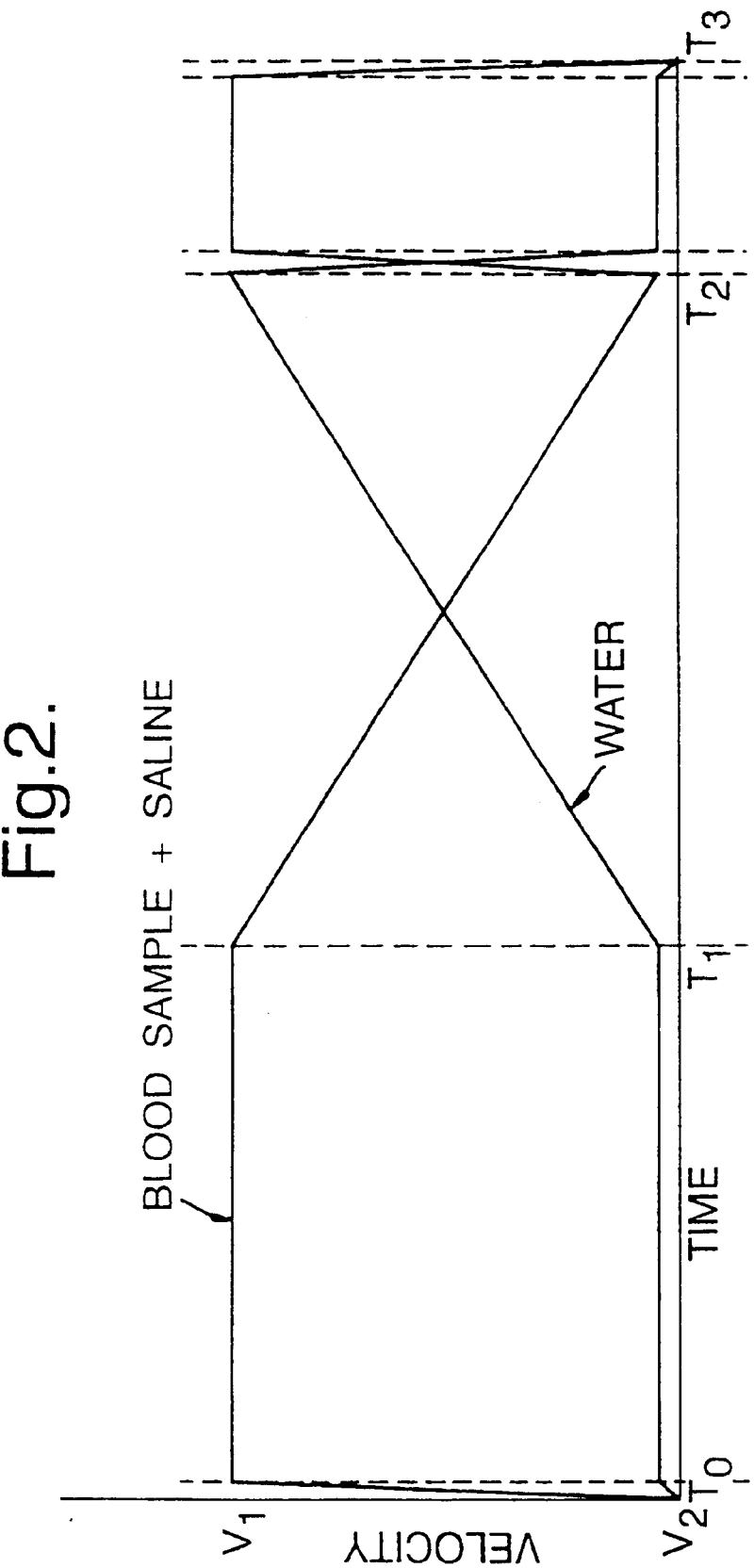
FIG. 2 shows velocity profiles for the discharge of fluids from fluid delivery syringes of a gradient generator section of the instrument of FIG. 1.

FIG. 2 shows how the velocity of the fluid discharged from each of the first and second fluid delivery syringes is varied with time to achieve a predetermined continuous gradient of osmolality of the sample suspension exiting the mixing chamber 19 along fluid line 24. The flow rate of the sample suspension is typically in the region of 200 $\mu$l s$^{-1}$ which is maintained constant whilst measurements are being made. This feature is described in detail in the Applicant's co-pending application (Agent's reference 62/2684/01). As shown in FIG. 2, a cam profile associated with a cam which drives fluid delivery syringe 21 accelerates the syringe plunger to discharge the sample at a velocity $V_1$, whilst a cam profile associated with a cam which drives fluid delivery syringe 17 accelerates the associated syringe plunger to discharge fluid at a lower velocity $V_2$. Once a constant flow rate from each delivery syringe has been established at time $T_0$, at time $T_1$ the cam profile associated with fluid delivery syringe 21 causes the rate of sample discharge to decelerate linearly over the period $T_2$-$T_1$ to a velocity $V_2$, while simultaneously, the cam profile associated with fluid delivery syringe 17 causes the rate of fluid discharge to accelerate linearly to velocity $V_1$. During this period, the combined flow rate of the two syringes remains substantially constant at around 200 $\mu$ls$^{-1}$ Finally, the two syringes are flushed over the period $T_3$-$T_2$.

Once both the first fluid delivery syringe 17 and the second fluid delivery syringe 21 have discharged their contents, the first delivery syringe is refilled with water in preparation for the next test. If a blood sample from a different subject is to be used, the second fluid delivery syringe 21 is flushed with saline from a saline supply via port #1 of multi-position distribution valve 22 to clean the contaminated body of the syringe.

The sample suspension which exits the mixing chamber 19 passes along fluid line 24 to the sensor section 3. A suitable sensor section is described in detail in the Applicant's co-pending International application also filed this day (Agent's reference 62/2681/03). The sample suspension passes to a sensing zone 25 comprising an electrical field generated adjacent an aperture through which the individual cells of the sample suspension must pass. As individual blood cells of the sample suspension pass through the aperture the response of the electrical field to the electrical resistance of each individual cell is recorded as a voltage pulse. The amplitude of each voltage pulse together with the total number of voltage pulses for a particular interrupt period, typically 0.2 seconds, is also recorded and stored for subsequent analysis including a comparison with the osmolality of the sample suspension at that instant which is measured simultaneously. The osmolality of the sample suspension may also be determined without measurement from a knowledge of the predetermined continuous osmotic gradient generated by the gradient generator section 2. As described below, the osmolality (pressure) is not required to determine the cell parameters.

Figure 3:
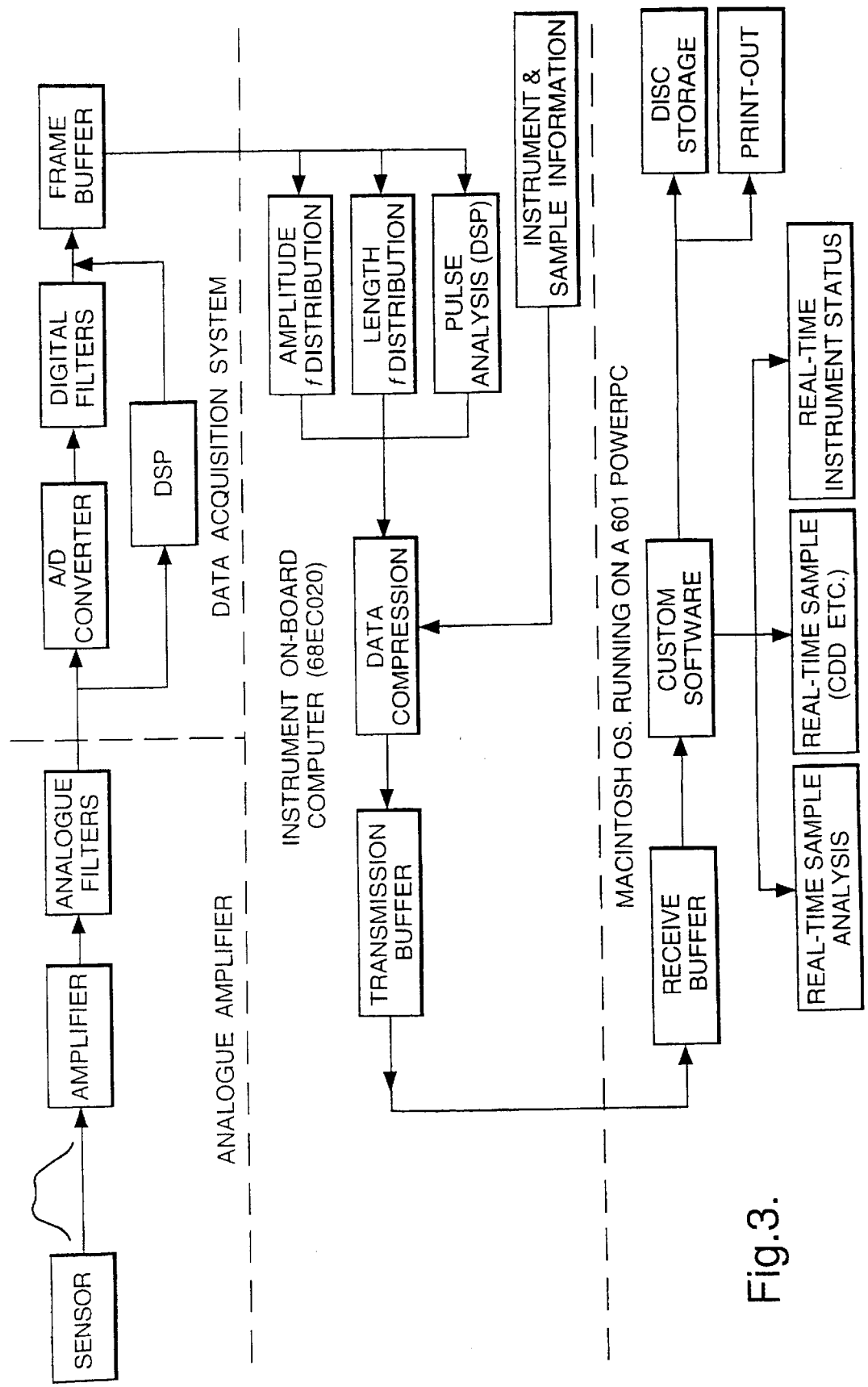
FIG. 3 shows a block diagram illustrating the data processing steps used in the instrument of FIG. 1.

FIG. 3 shows how data is collected and processed. Inside each instrument is a main microprocessor which is responsible for supervising and controlling the instrument, with dedicated hardware or low-cost embedded controllers responsible for specific jobs within the instrument, such as operating diluters, valves, and stepper motors or digitizing and transferring a pulse to buffer memory. The software which runs the instrument is written in C and assembly code and is slightly less than 32 K long.

When a sample is being tested, the amplitude and length of each voltage pulse produced by the sensor is digitized to 12-bit precision and stored in one of two 16K buffers, along with the sum of the amplitudes, the sum of the lengths, and the number of pulses tested. Whilst the instrument is collecting data for the sensors, one buffer is filled with the digitized values while the main microprocessor empties and processes the full buffer. This processing consists of filtering out unwanted pulses, analysing the data to alter the control of the instrument and finally compressing the data before it is sent to the personal computer for complex analysis.

Optional processing performed by the instrument includes digital signal processing of each sensor pulse so as to improve filtering, improve the accuracy of the peak detection and to provide more information about the shape and size of the pulses. Such digital signal processing produces about 25 16-bit values per cell, generating about 25 megabytes of data per test.

Data processing in the personal computer consists of a custom 400K program written in C and Pascal. The PC displays and analyses the data in real time, controls the user interface (windows, menus, etc.) and stores and prints each sample.

The software also maintains a database of every sample tested enabling rapid comparison of any sample which has been previously tested. Additionally, the software monitors the instrument's operation to detect malfunctions and errors, such as low fluid levels, system crashes or the user forgetting to turn the instrument on.

Figure 4:
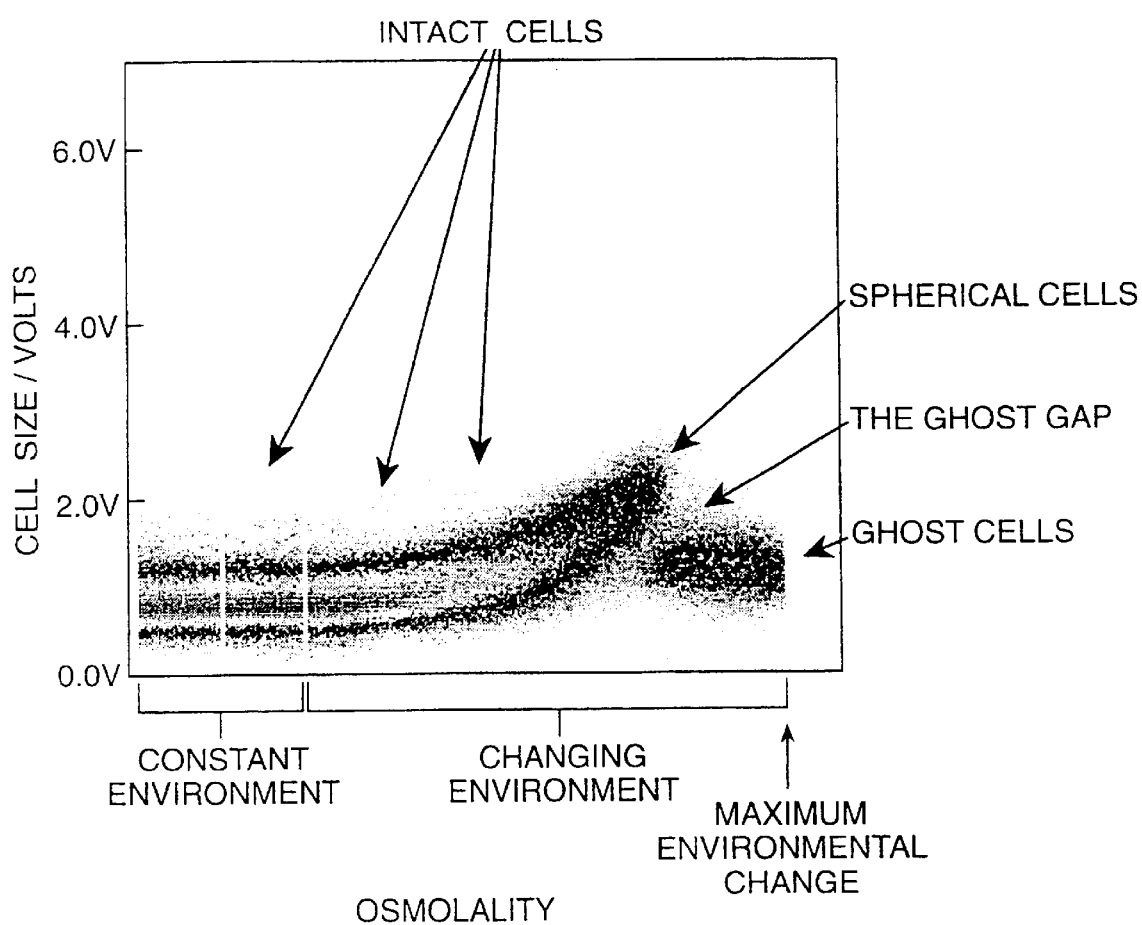
FIG. 4 shows an example of a three-dimensional plot of osmolality against measured voltage for cells of a blood sample analyzed in accordance with the present invention.
Figure 5:
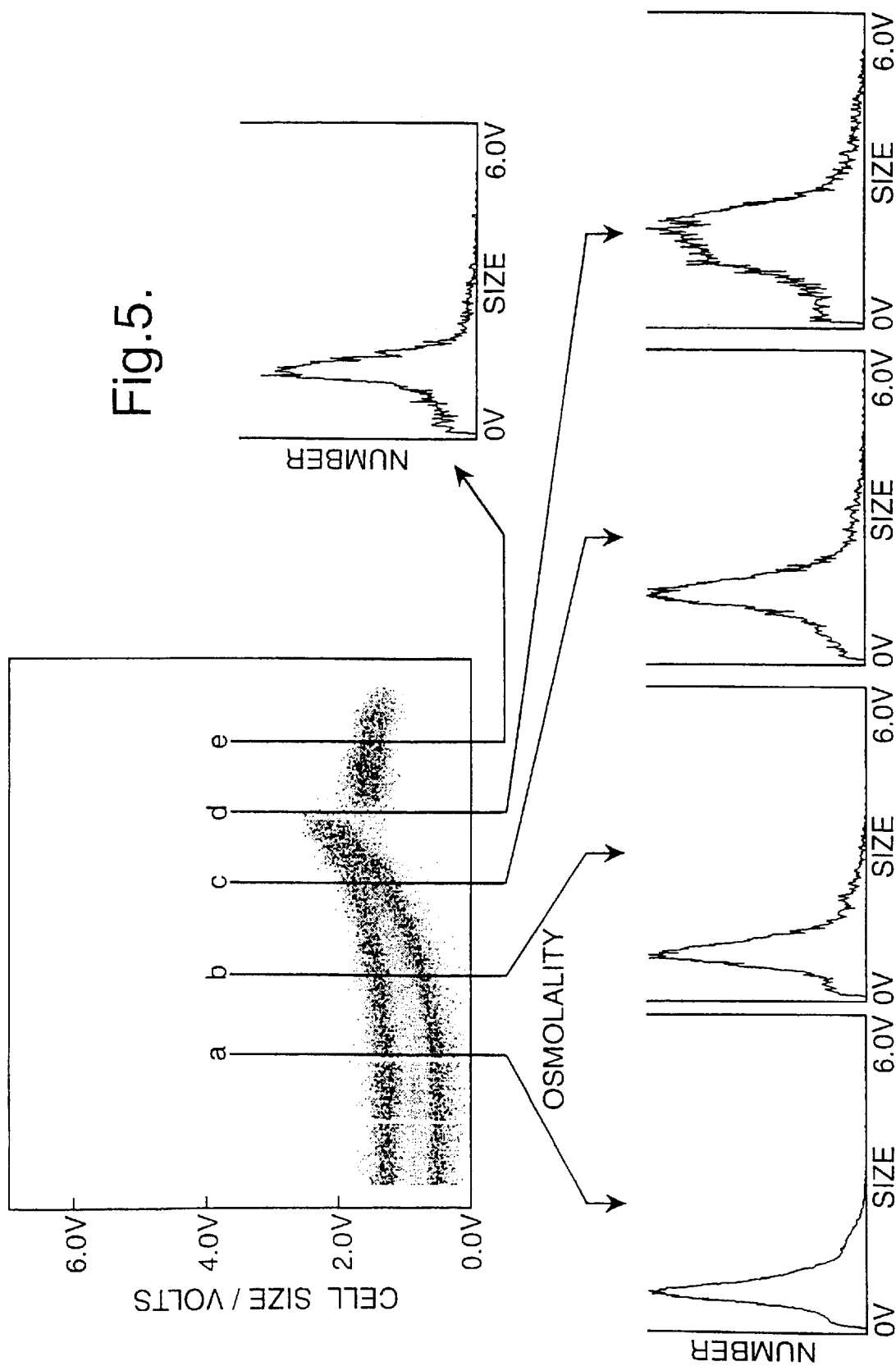
FIG. 5 shows another example of a three-dimensional plot of osmolality against measured voltage which illustrates the frequency distribution of blood cells at intervals.

The voltage pulse generated by each cell of the sample suspension as it passes through the aperture of sensing zone 25 is displayed in graphical form on a VDU of a PC as a plot of osmolality against measured voltage. The sample suspension passes through the sensor section at a rate of 200 $\mu$ls$^{-1}$. The second dilution step is controlled to achieve an initial cell count of around 5000 cells per second, measured at the start of any test, so that in an interrupt period of 0.20 seconds, around 1000 cells are detected and measured. This is achieved by varying automatically the volume of saline discharged by the diluter pump 7 from the fluid line 12 in the second dilution step. Over a test period of 40 seconds, a total of 200 interrupt periods occur and this can be displayed as a continuous curve in a three-dimensional form to illustrate the frequency distribution of measured voltage at any particular osmolality, an example of which is shown in FIGS. 4 and 5.

The measured cell voltage, stored and retrieved on an individual cell basis is shown displayed on a plot of voltage against the osmolality of the solution causing that voltage change. Using individual dots to display the measured parameter change for each individual cell results in a display whereby the distribution of cells by voltage, and thereby by volume, in the population is shown for the whole range of solutions covered by the osmolality gradient. The total effect is a three-dimensional display shown as a measured property change in terms of the amplitude of the measured voltage pulses against altered parameter, in this case the osmolality of the solution, to which the cells have been subjected and the distribution or density of the cells of particular sizes within the population subjected to the particular osmolality. The effect is to produce a display analogous to a contour map, which can be intensified by using colour to indicate the areas of greatest intensity.

When full data is available on the distribution of cell size in a particular population of cells subjected to haemolytic shock in a wide range of hypotonic solutions, at osmolalities just below a critical osmolality causing lysis a gap in the populations is visible. As shown in FIG. 4, ghost cells are fully visible or identifiable in the three-dimensional plot and the unruptured cells are clearly identifiable, but between them is a region defined by osmolality and cell volume where relatively few individuals appear. The existence of this phenomenon, which we have termed the "ghost gap", has not previously been recognised.

Figure 6:
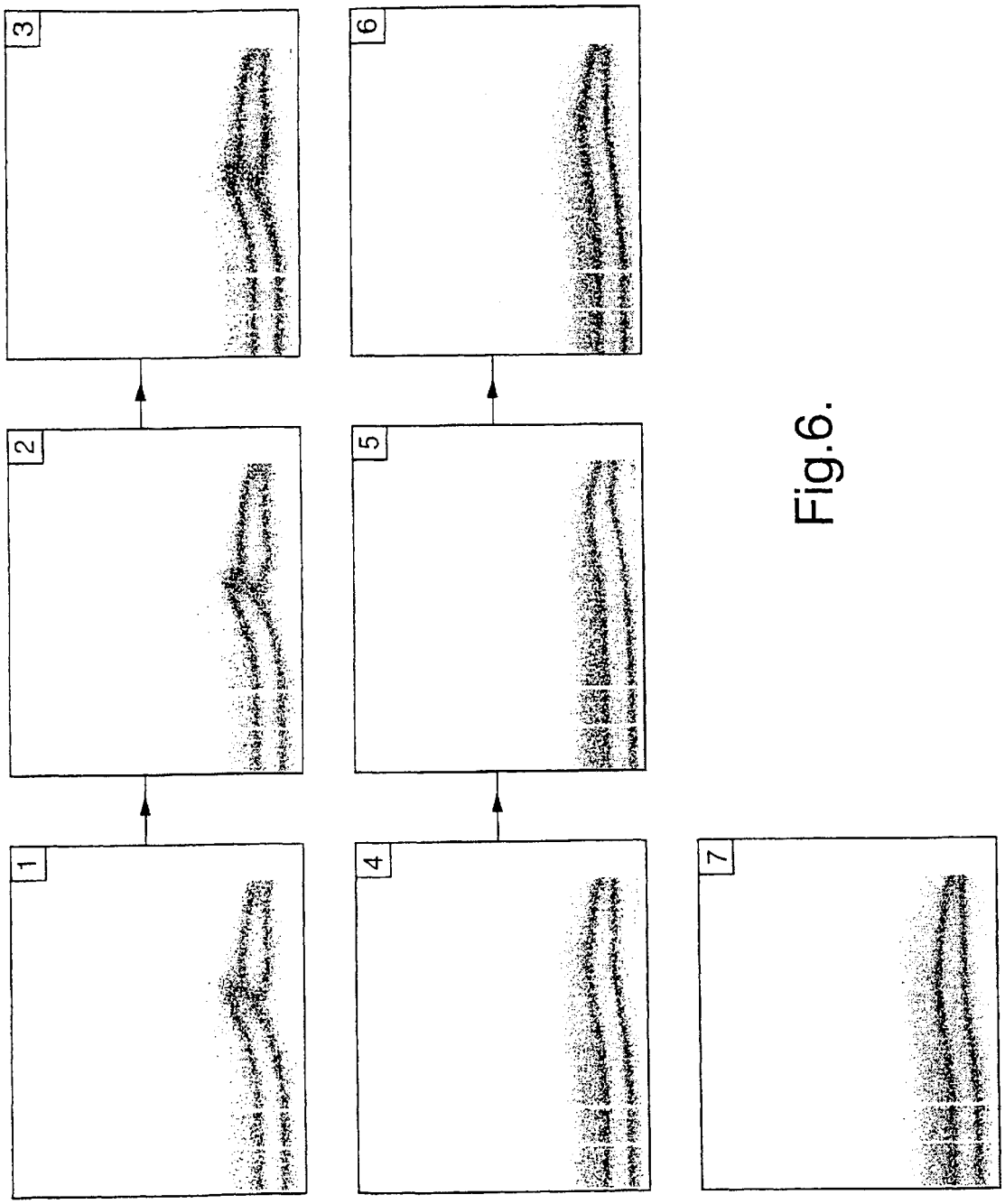
FIG. 6 shows a series of three-dimensional plots for a sample tested at hourly intervals.

If the entire series of steps are repeated at timed intervals on further aliquots of the original sample and the resulting measured voltage is plotted against osmolality, time and frequency distribution, a four-dimensional display, is obtained which may be likened to a change in weather map. This moving three-dimensional display, its motion in time being the fourth dimension, provides an additional pattern characteristic of a particular blood sample. This is shown in the series of images in FIG. 6. The images shown in FIG. 6 are the results of tests carried out at hourly intervals at a temperature of 37° C. As the measurements are so exact, the repeat values are superimposable using computer sequencing techniques.

As shown, cells slowly lose their ability to function over time, but they also change in unexpected ways. The size and shape of the cells in a blood sample change in a complex, non-linear but repeatable way, repeating some of the characteristic patterns over the course of days and on successive testing. The patterns, emerging over time, show similarity among like samples and often show a characteristic wave motion. The pattern of change may vary between individuals reflecting the health of the individual, or the pattern may vary within a sample. Thus a sample that is homogeneous when first tested may split into two or several subpopulations which change with time and their existence can be detected by subjecting the sample to a wide range of different tonicities and recording the voltage pulse in the way described. As shown in FIG. 6, after the first few hours the cell becomes increasingly spherical in the original sample, it then becomes flatter for several hours, then more spherical again, reaches a limit, and then becomes thinner and finally may swell again. It has been determined that the rate at which observed changes take place are influenced by pH, temperature, available energy and other factors.

The three-dimensional pattern provides data which enables identification of the precise osmolality at which particular cells reach their maximum volume, when they become spheres. With appropriate calibration, which is described in detail below, and using the magnitude of the voltage pulse, it is possible to define precisely and accurately the actual volume of such cells and thereafter derive a number of other cell parameters of clinical interest.

The amplitude of the voltage pulses produced by the sensor 25 as individual cells pass through the electrical field are proportional to the volume of each cell. However, before a conversion can be performed to provide a measure of cell volume, the instrument requires calibration. This is performed using spherical latex particles of known volume and by comparison with cell volumes determined using conventional techniques.

Figure 7:
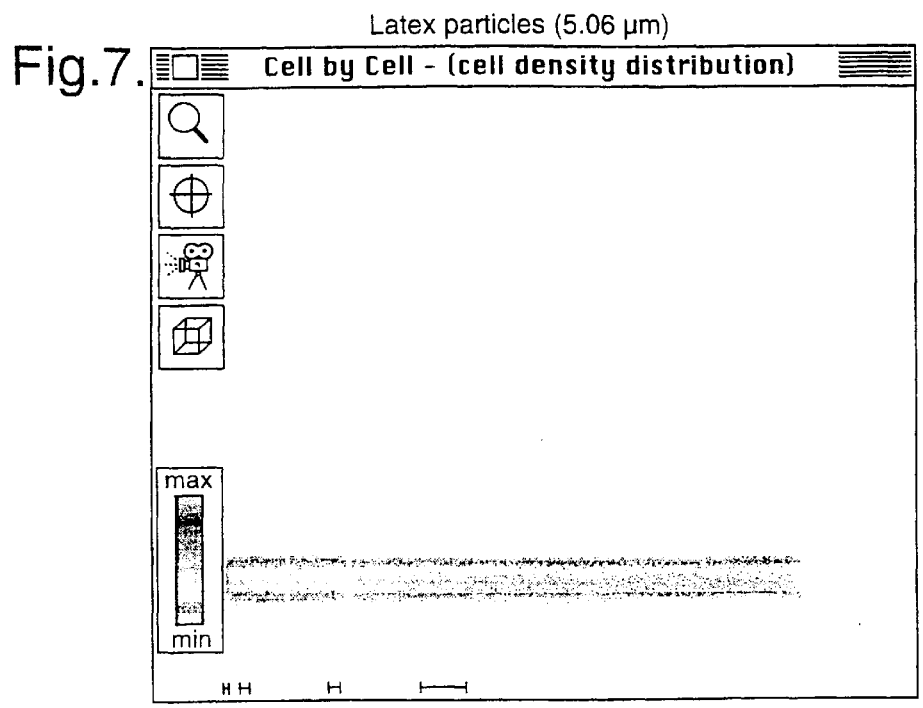
FIGS. 7 and 8 show results for spherical latex particles as part of an instrument calibration routine.
Figure 8:
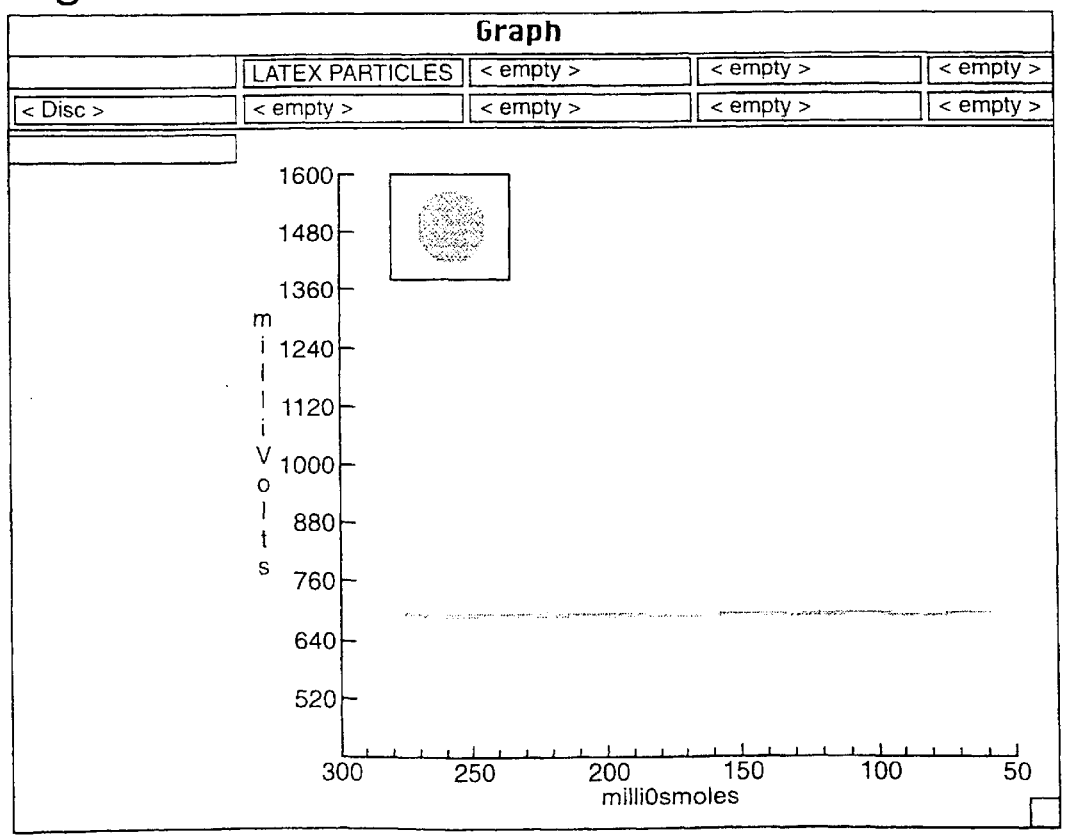

Experimental results have shown that the mapping of measured voltage to spherical volume of commercially available latex particles is a linear function. Accordingly, only a single size of spherical latex particles needs to be used to determine the correct conversion factor. In a first calibration step, a sample containing latex particles manufactured by Bangs Laboratories Inc. having a diameter of 5.06 μm i.e. a volume of 67.834 m³, was sampled by the instrument. The three-dimensional plot for the latex particles is shown in FIG. 7 with a plot of osmolality against mean voltage shown in FIG. 8. In this particular test, the instrument produced a mean voltage of 691.97 mV. The spherical volume is given by the equation:

Spherical volume=measured voltage×$K_{volts}$ where $K_{volts}$ is the voltage conversion factor. Re-arranging this equation gives:

$$K_{volts} = \frac{\text{spherical volume}}{\text{measured voltage}}$$

which in this case gives, $$K_{volts} = \frac{67.834}{691.97} = 0.0980$$

This value of $K_{volts}$ is only valid for the particular instrument tested and is stored in a memory within the instrument.

In a second calibration step, a shape correction factor is determined to take account of the fact that the average blood cell in the average individual has a bi-concave shape. Applying the above voltage conversion factor $K_{volts}$ assumes that, like the latex particles, blood cells are spherical and would therefore give an incorrect cell volume for cell shapes other than spherical. In the present invention, a variable shape correction function is determined so that the mean volume of the blood cells at any osmolality up to the critical osmolality causing lysis can be calculated extremely accurately.

Figure 9:
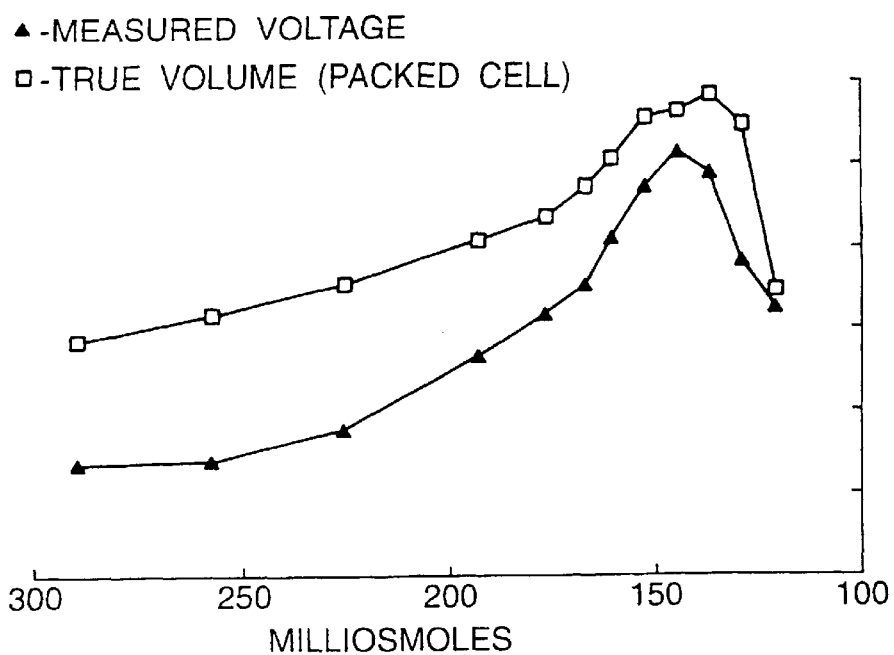
FIG. 9 shows superimposed plots of osmolality (x-axis) against measured voltage and true volume, respectively.

To illustrate this, a sample was tested at a number of accurately known osmolalities and the volume of the blood cells measured using a standard reference method, packed cell volume. A portion of the same sample was also tested by the method of the present invention using the instrument of FIG. 1 to measure the voltage pulses from individual cells at the corresponding osmolalities. The results of these procedures are shown in Table 1 and plotted as two superimposed graphs of osmolality (x-axis) against measured voltage and true volume, respectively, in FIG. 9.

At an isotonic osmolality of 290 mosm, the true volume, as determined by the packed cell volume technique, was 92.0 fl, whilst the measured mean voltage was 670 mV.

The true isotonic volume of the cells is given by equation:

Volume$_{iso}$=Voltage$_{iso}$×$K_{volts}$×$K_{shape}$ where Voltage$_{iso}$ is the measured voltage and $K_{shape}$ is a shape correction factor.
Re-arranging:

$$K_{shape} = \frac{\text{Volume}_{iso}}{\text{Voltage}_{iso} \times K_{volts}}$$

which in this example gives, $$K_{shape} = \frac{92.0}{670 \times 0.0980} = 1.4$$

Table 1 shows the shape correction factor $K_{shape}$ for each of the other aliquots and demonstrates that the factor to be applied to each sample is different with the maximum shape correction being applied at isotonic osmolalities where the blood cells are bi-concave rather than spherical. To automate the calculation of $K_{shape}$ at any osmolality of interest a shape correction function is required. The following general function describes a shape correction factor based on any two sensor readings i.e. measured voltages:

$f(K_{shape})=f$ (SR1, SR2)

where SR1 is a sensor reading (measured voltage) at a known shape, typically spherical, and SR2 is a sensor reading (measured voltage) at an osmolality of interest, typically isotonic.

Analysis has shown that this is a linear function and that:

$$f(K_{shape}) = 1 + \left[\frac{(SR1 - SR2)}{(SR1)}\right] \times K_a$$

where $K_a$ is an apparatus dependent constant, which is determined as follows:
$K_{shape}$ at an osmolality of 290 mosm is known (see above), applying the values SR1=1432 mV, SR2=670 mV and $K_{shape}$=1.4 to the above equation gives:

$$1.4 = 1 + \left[\frac{(1432 - 670)}{1432}\right] \times K_a$$

re-arranging:
$K_a$=0.7518
This value of $K_a$ is constant for this instrument.

The true isotonic volume of a blood sample is determined by comparing the measured voltage at an isotonic volume of interest with the measured voltage of cells of the same blood sample at some known or identifiable shape, most conveniently cells which have adopted a spherical shape, whereby:

$$\text{Volume}_{iso} = \text{Voltage}_{iso} \times K_{volts} \times f(K_{shape})$$

$$= SR2 \times 0.0980 \times \left[1 + \left[\frac{(SR1 - SR2)}{SR1}\right] \times 0.7518\right]$$

Figure 10A:
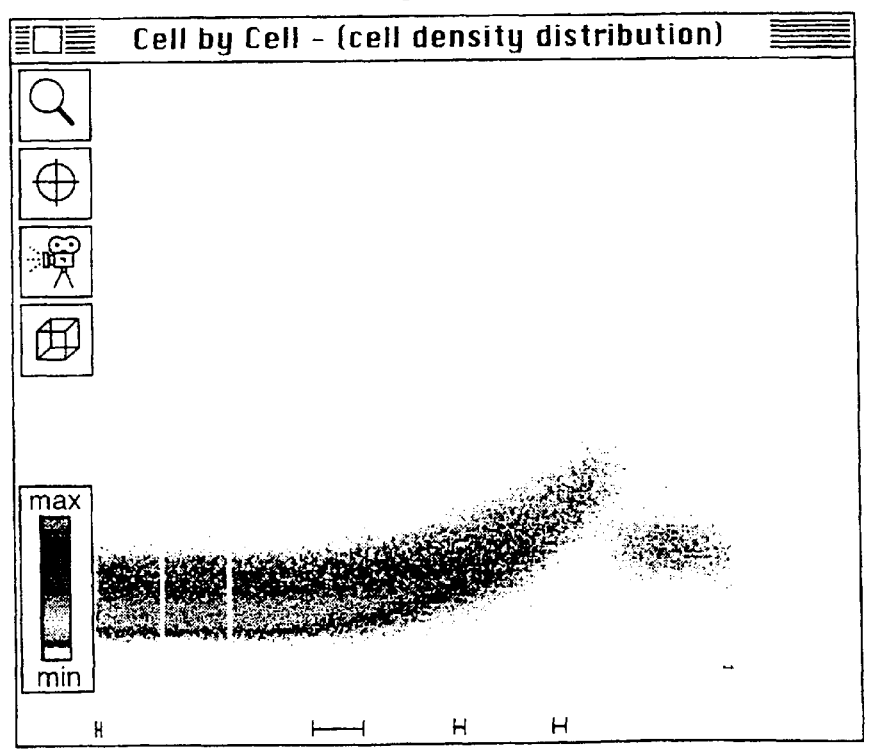
Figure 10B:
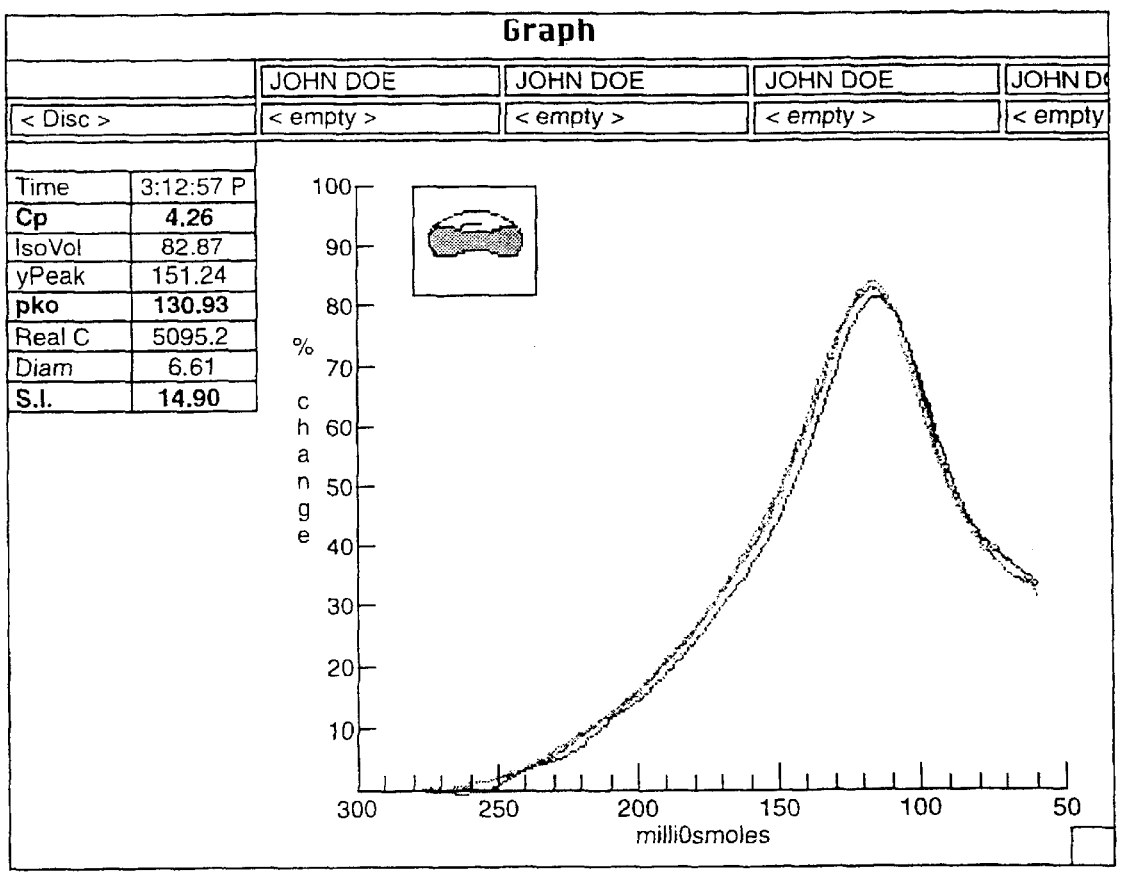
Figure 10D:
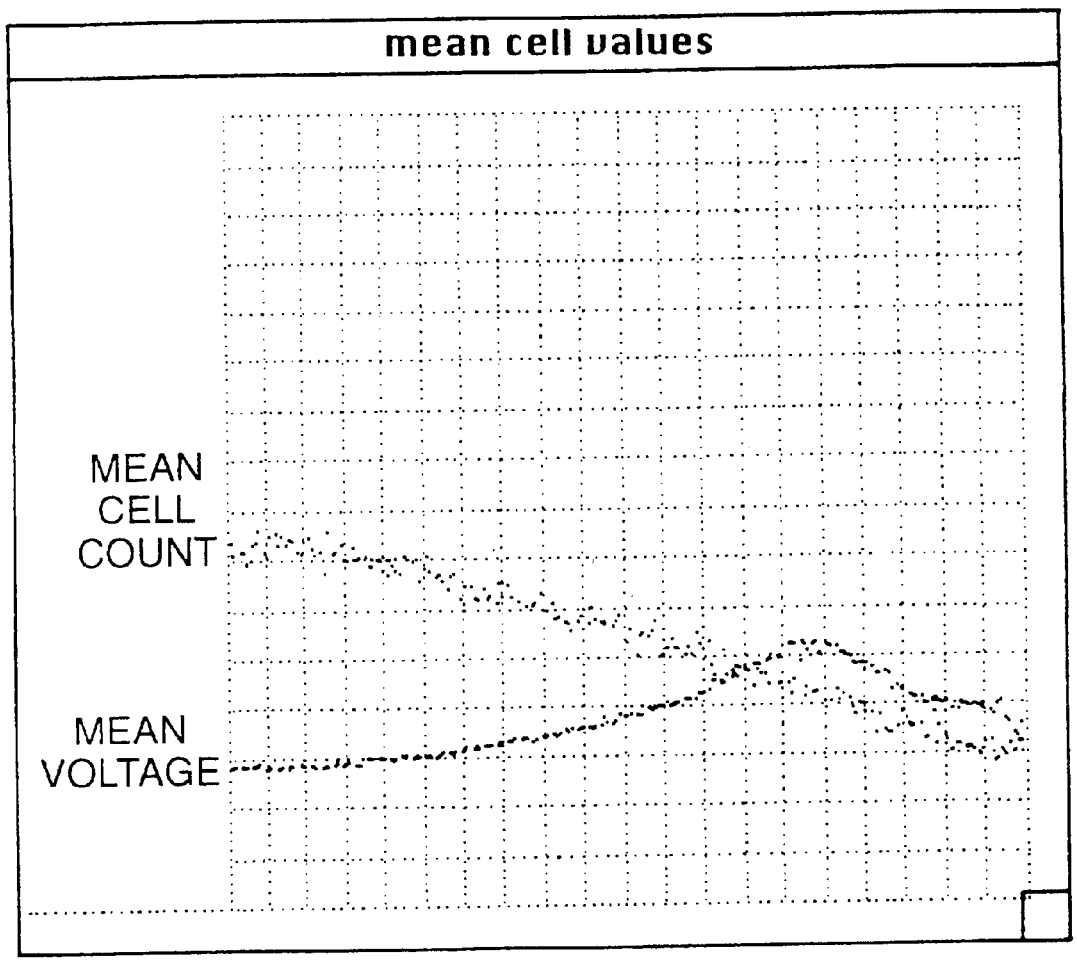
Figure 11:
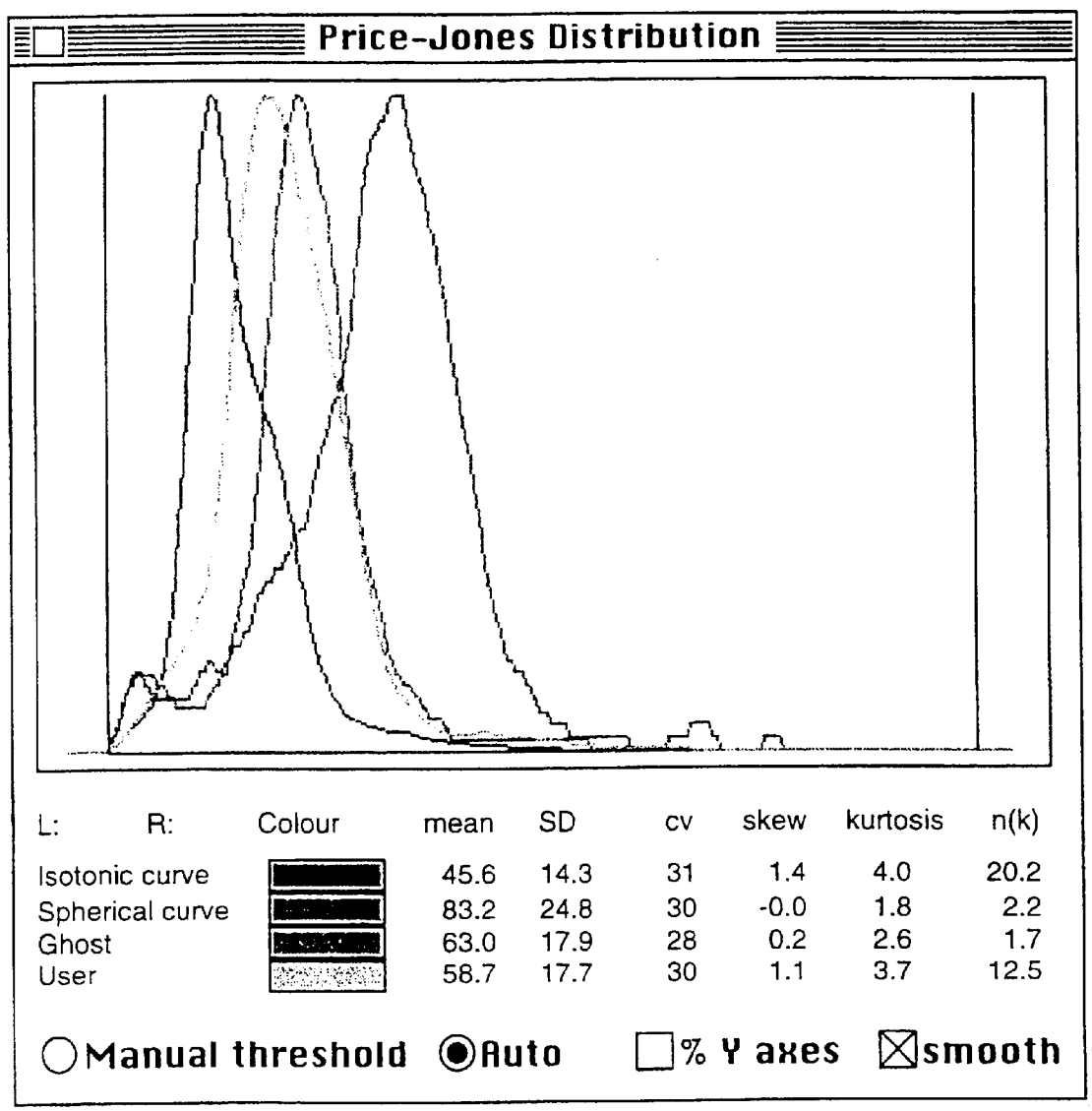
FIG. 11 shows Price-Jones curves of the results shown in FIGS. 10*a* to 10*d*.

In the present invention, the point at which the blood cells become spherical when subjected to a predetermined continuous osmotic gradient can be determined very accurately. FIGS. 10a–10d show the results for a normal blood sample from a healthy individual. FIG. 10a shows a three-dimensional plot of measured voltage against osmolality, FIG. 10b shows a graph of osmolality against percentage change in measured voltage for a series of tests of a sample, FIG. 10c shows the results in a tabulated form, and FIG. 10d shows superimposed graphs of mean voltage and cell count for the test, respectively, against osmolality. As shown, the cell count, which is initially 5000 cells per second at the beginning of a test, reduces throughout the test due to the dilution of the sample in the gradient generator section 2. The mean voltage rises to a maximum at a critical osmolality where the blood cells achieve a spherical shape and then reduces. Using standard statistical techniques, the maxima of the curve in FIG. 10b, and therefore the mean voltage at the maxima, can be determined. The mean voltage at this point gives the value SR1 for the above equation. It is then possible to select any osmolality of interest, and the associated measured voltage SR2, and calculate the true volume of the cell at that osmolality. Typically, the isotonic osmolality is chosen, corresponding to approximately 290 mosm.

For the above test, at 290 mosm, SR1=1432 mV and SR2=670 mV. Accordingly:

$$f(K_{shape})_{290} = 1 + \left[\frac{1432 - 670}{1432}\right] \times 0.7518$$

$K_{shape\ 290} = 1.40$
and therefore:

$$Volume_{iso} = SR2 \times K_{volts} \times K_{shape}$$
$$= 670 \times 0.0980 \times 1.40$$
$$= 91.92\ fl,$$

and:

$$Volume_{sph} = SR1 \times K_{volts} \times K_{shape}$$
$$= 1432 \times 0.098 \times 1.0$$
$$= 140.34\ fl.$$

and:

$Volume_{sph} = SR1 \times K_{volts} \times K_{shape} = 1432 \times 0.098 \times 1.0 = 140.34$ fl.

Knowledge of the mean volume of the sphered cells allows calculation of spherical radius as:

$$Volume_{sph} = \frac{4\pi r^3}{3}$$

from which the spherical radius $$r = \left[\frac{3 \times Volume_{sph}}{4\pi}\right]^{\frac{1}{3}}$$
$$r = \left[\frac{3 \times 140.34}{4\pi}\right]^{\frac{1}{3}}$$
$$= 3.22\ \mu m$$

Having determined volume$_{iso}$, volume$_{sph}$ and the spherical cell radius, it is possible to calculate a number of other parameters. In particular:

1. Surface Area (SA)

Since the surface area SA is virtually unchanged at all osmolalities, the cell membrane being virtually inelastic, and in particular between spherical and isotonic, the surface area SA may be calculated by substituting r into the expression:

$$SA = 4\pi r^2$$
$$= 4\pi x (3.22)^2$$
$$= 130.29\ \mu m^2$$

2. Surface Area to Volume Ratio (SAVR)

Given that the walls of a red cell can be deformed without altering their area, once the surface area SA is known for a cell or set of cells of any particular shape, the surface area is known for any other shape, thus the surface area to volume ratio SAVR can be calculated for any volume. SAVR is given by the expression:

$$SAVR = \frac{4\pi r^2}{Volume_{iso}}$$
$$= \frac{SA}{Volume_{iso}}$$
$$= \frac{130.29}{91.99}$$
$$= 1.42$$

3. Sphericity Index (SI)

The present invention can easily measure the SAVR, a widely quoted but hitherto, rarely measured indication of cell shape. For a spherical cell, it has the value of 3/r, but since cells of the same shape but of different sizes may have different SAVR values, it is desirable to use the sphericity index SI which is a dimensionless unit independent of cell size, given by the expression:

$$SI = SAVR \times \frac{r}{3}$$
$$= 1.52$$
$$= 1.42 \times \frac{3.22}{3}$$

4. Cell Diameter (D)

When the normal cell is in the form of a bi-concave disc at isotonic osmolality, it is known that the ratio of the radius of a sphere to that of the bi-concave disc is 0.8155. On this basis, therefore, the diameter D of a cell in the form of a bi-concave disc is given by:

$$D = \frac{2r}{0.8155}$$
$$= \frac{2 \times 3.22}{0.8155}$$
$$= 8.19\ \mu m$$

The same parameter can be determined for all other osmolalities. The frequency distribution of the cell diameters is given both as dispersion statistics as well as a frequency distribution plot. The present invention provides an automated version of the known manual procedure of plotting a frequency distribution of isotonic cell diameters known as a Price-Jones curve. The present invention is capable of producing a Price-Jones curve of cell diameters for any shape of cell and, in particular, isotonic, spherical and ghost cells (at any osmolality) and is typically based on 250,000 cells. This is shown in FIG. 10.

5. Cell Thickness (CT)

When the cell is in the form of a bi-concave disc, an approximate measure of the cell thickness can be derived from the cross-sectional area and the volume. The area is of course derivable from the radius of the cell in spherical form. The cell thickness can therefore be calculated as follows:

$$CT = \frac{Volume_{iso}}{\pi r^2}$$

$$= \frac{91.92}{\pi \times 3.22^2}$$

$$= 2.82 \ \mu m$$

6. Surface Area per millilitre (SAml)

The product of the surface area (SA) and the cell count (RBC) is the surface area per millilitre (SAml) available for physiological exchange. The total surface area of the proximal renal tubes that are responsible for acid-base regulation of the body fluids is 5 m². The total surface area of the red blood cells that also play an important part in the regulation of the acid-base balance is 4572 m², almost 3 orders of magnitude larger. RBC is calculated internally from a knowledge of the flow rate of the diluted blood sample, a cell count for each sample and the dilution of the original whole blood sample. Typically, RBC is approximately $4.29 \times 10^9$ red cells per ml.

$$SA \ ml = SA \times RBC \ (\text{per ml})$$

$$= 130.29 \ \mu m^2 \times 4.29 \ 10^9$$

$$= 0.56 \ m^2 \ ml^{-1}$$

7. Cell Permeability (Cp)

Figure 12:
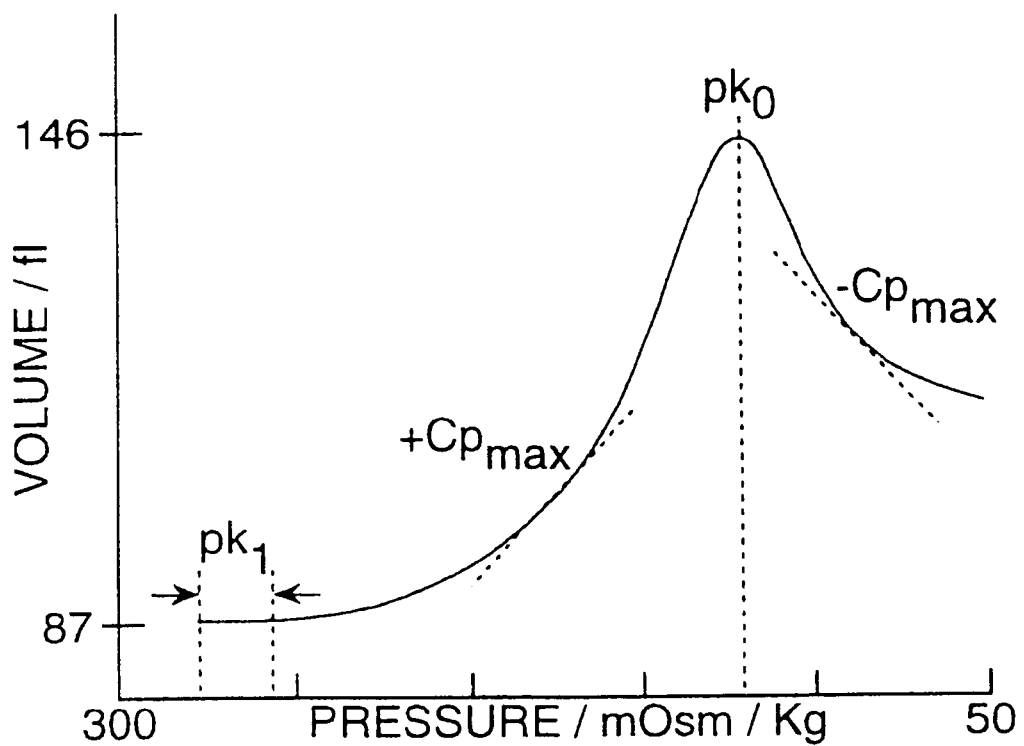
FIG. 12 shows a graph of osmolality against cell volume and indicates a number of different measures of cell permeability.

The plot of cell volume against osmolality in FIG. 12 reveals a characteristic curve showing how the cell volume changes with decreasing osmolality and indicates maximum and minimum rates of flow across the membrane and the flow rates attributed to a particular or series of osmotic pressures. Many of the cell permeability measurements are primarily dependent upon the change in volume of the cells at different pressures. Table 2 shows the volume measurements produced by the method of the invention and the change in volume at each mosm. Such a table is calculated automatically from continuous functions and is not usually seen by the user. The results are shown plotted as a graph of net fluid exchange against osmotic pressure in FIG. 13.

Having obtained measures of osmotic pressure ($P_{osm}$), cell volume, surface area (SA) and other relevant environmental factors, it is possible to obtain a number of measures of cell permeability:

a) Cp Rate

This coefficient of permeability measures the rate of fluid flow across a square meter of membrane in response to a specified pressure. All positive rates represent a net flow into the cell, while all negative rates are the equivalent of a net flow out of the cell. The rate is determined by:

$$Cp \ rate = \Delta cell \ volume / \Delta P_{osm}/SA \ at \ S.T.P.$$

Figure 13:
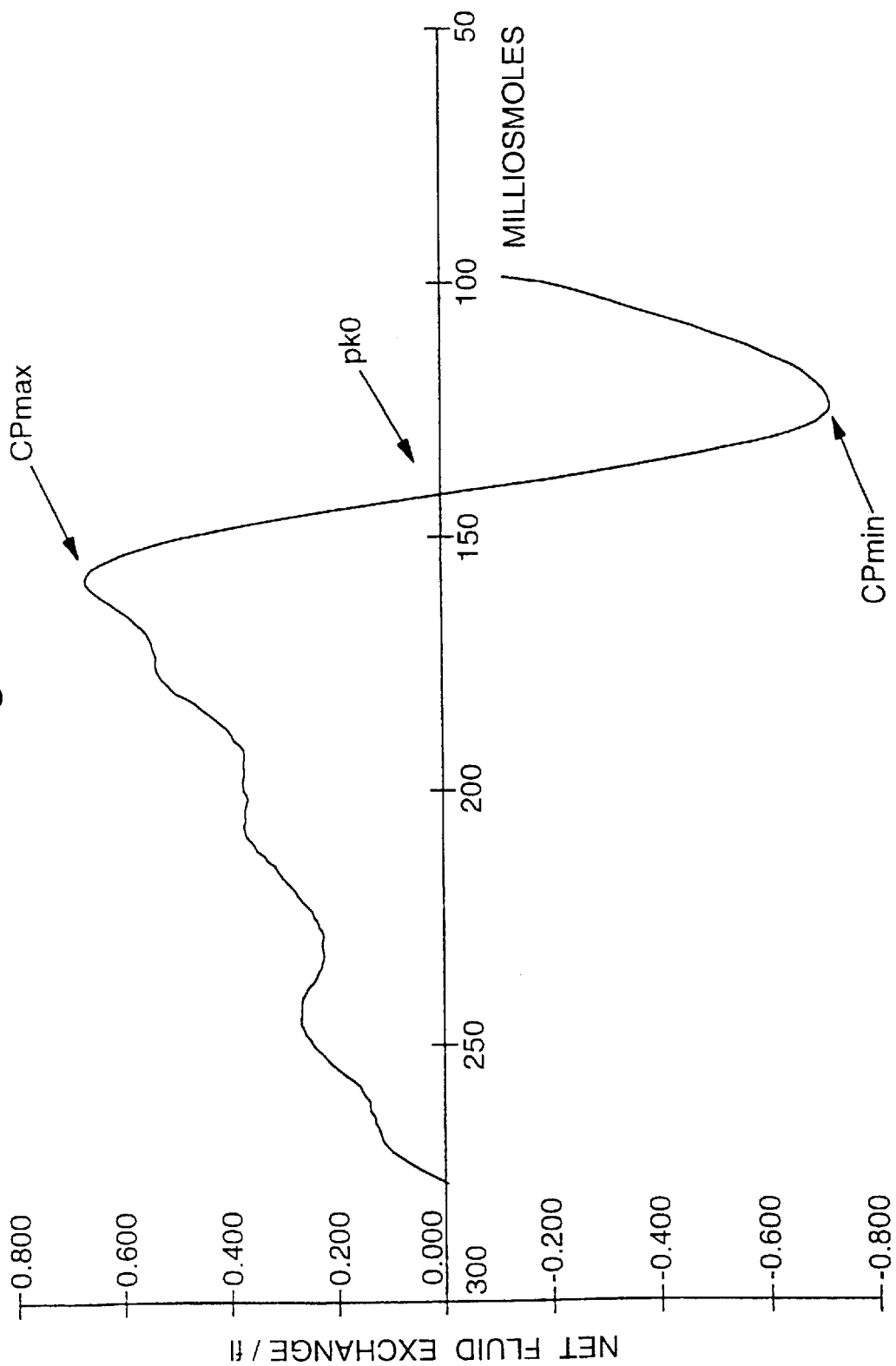
FIG. 13 shows a graph of osmolality against net fluid flow.

Using the discrete values from Table 2 and FIG. 13, the Cp rate between 200 and 141 mOsm is given as:

$$Cp \ rate_{290.141} = (139.94 - 93.98)/(141 - 290)/130.29 \ \mu m^2$$

$$= 45.96 \ fl/149 \ mOsm/130.29$$

$$= 2.36 \times 10^{-3} \ fl/mOsm/\mu m^2$$

$$= 2.36 \times 10^9 \ fl/mOsm/m^2$$

$$= 2.36 \ ml/mOsm/m^2$$

b) Permeability Constant $pk_n$

This set of permeability measures describe each pressure where the net permeability rate is zero, and are numbered $pk_0, pk_1 \ldots pk_n$.

(i) $pk_0$ coincides with the minimum absolute pressure (hypotonic) to which a cell can be subjected without loss of integrity and is shown in FIG. 12. A pressure change of one tenth of a milliosmole per kg (0.0001 atms) at $pk_0$ produces a change in permeability of between one and two orders of magnitude making $pk_0$ a distinct, highly reproducible measure.

(ii) $pk_1$ is a measure of the cells' ability to volumetrically regulate in slightly hypotonic pressures and is also shown in FIG. 12. After a certain pressure, the cell can no longer defeat the osmotic force, resulting in a change in the cell's volume. $pk_1$ provides a measure of the cells ability to perform this regulation, thereby measuring a cell's maximum pump transfer capability.

(iii) $pk_2$, a corollary of $pk_1$, is a measure of the cells ability to volumetrically regulate in hypertonic pressures, and occurs at low differential pressures, when compared to the cell's typical in vivo hydrostatic pressure (not shown).

The permeability constant $pk_n$ is described by the following equation:

$$pk_n = \Delta P_{osm}/SA \ at \ S.T.P.$$

When calculating $pk_0$, $\Delta P_{osm}$=(isotonic pressure)–(pressure where net flow is zero).

When calculating $pk_1$, $\Delta P_{osm}$=(isotonic pressure)–(first hypotonic pressure where net positive flow begins). The calculation of Pk, (not shown) is identical to $pk_1$, except $\Delta P_{osm}$ measures the first hypertonic pressure where net positive flow is not zero.

Using the discrete values from Table 2 and FIG. 13, $$pK_o = 141.5 \ mOsm \ Kg^{-1}/130 - 29 \ \mu m^2$$

$$= 1.086$$

c) CPΔ

This dimensionless value is the comparison of any two Cp rates, and is expressed as the net amount of fluid to cross the cell membrane between any two pressures. It provides a volume independent and pressure dependent comparison of permeability rates. This measure may be used to compare permeability changes in the same individual over a period ranging from minutes to months.

From CP rate above, CP rate$_{290.141}$ was determined to be 2.41 ml/mOsm/m².

$$CP\Delta = (CP \ rate \ 1 - CP \ rate \ 2/CP \ rate \ 2) \times 100$$

$$CP\Delta = (2.41 - 2.36)/2.36 \times 100$$

$$= 2.07\% \ change$$

d) $Cp_{max}$

This is the maximum rate of flow across the cell's membrane. For almost all cells, there are two maxima, one positive (net flow into the cell) and one negative (net flow out of the cell) situated either side of $pk_0$. $Cp_{max}$ is determined by detecting the maximum positive and negative gradients of the continuous curve of change in cell volume against osmolality. From the results, $Cp_{max}$ into the cell is +0.670 fl/mOsm and $Cp_{max}$ out of the cell is −0.722 fl/mOsm.

e) Membrane Structural Resistance (MSR)

This is a measure of the structural forces inside a cell which resist the in-flow or out-flow of water. It is determined by the ratio of $Cp_{max}$ to all other non-zero flow rates into the cell. As the membrane is theoretically equally permeable at all pressures, change from the maximum flow rate outside the pressure range of $pk_1$ to $pk_2$ are due to mechanical forces. It is clear that $pk_0$ is an entirely mechanical limit on the cell because as $Cp_{rate}$ approaches zero, MSR approaches ∞, thereby producing more strain than the membrane can tolerate.

$$MSR = Cp_{max}/Cp_{rate} \times 100\%$$

f) cpml

This is a measure of the physiological permeability available to an individual per unit volume of tissue or blood, or for the whole organ or total body, and is calculated by:

$$Cpml = \Delta \text{cell volume}/\Delta P_{osm}/m^3 \text{ per ml of whole blood.}$$

From the above calculations, in 1 ml there are $4.29 \times 10^9$ red cells each with a surface area of 130.29 $\mu m^2$ and $SAml = 0.56 \; m^2 \; ml^{-1}$ At $Cp_{max}$ (for instance) the flow rate into the cell was $$0.677 \; fl/130.29 \; \mu m^2 = 5.20 \times 10^{-3} \; fl/\mu m^2$$

Thus in 1 ml of whole blood the net volume of fluid crossing the membrane was $$= 5.20 \times 10^{-3} \; fl/\mu m^2 \times 0.559 \times 10^{12} \; \mu m/ml$$

$$= 2.91 \; ml/ml \text{ of whole blood}$$

h) $Cp_{net}$ $CP_{net}$ is defined as the rate at which fluid can be forced across a unit area of membrane at standard temperature and pressure over unit time and is a pressure independent measure of the coefficient of permeability, given by the equation:

$$CP_{net} = \frac{(Volume_{sph} - Volume_{iso})}{SA}$$
$$= \frac{140.34 - 91.92}{130.29}$$
$$= 0.372$$
$$= 3.72 \; ml \; m^{-2}$$

FIG. 14 illustrates the three-dimensional frequency distribution of a sample from a patient having an HbCC disease. As shown, the plot is grossly abnormal.

What is claimed is:

1. A method of testing a sample of cells suspended in a liquid medium to determine a measure of cell permeability of cells in the sample comprising:
   a) feeding the sample cell suspension into another liquid medium having a continuously changing osmolality gradient to produce an altered sample cell suspension by attempting to induce a flow of fluid across cell membranes and thereby change the shape of cells in the sample suspension;
   b) passing the altered cell suspension through a sensor;
   c) measuring a property of the altered sample cell suspension which is related to volume of the cells;
   d) recording a sensor measurement for the cells;
   e) subjecting the recorded sensor measurements to analysis to identify a value of the recorded measurement at which cells in the altered sample cell suspension achieve a spherical shape;
   f) determining the volume of the cells in the altered sample cell suspension based on analysis of the recorded measurements of step (e) and calculating the surface area of the cells from the volume determination; and
   g) calculating cell permeability as a measure of the volume of fluid which crosses cell membranes as the cells undergo a change in shape in response to continuously changing osmolality.

2. A method according to claim 1 wherein steps (e) through (g) are performed simultaneously.

3. A method according to claim 1 wherein the osmolality corresponding to the spherical shape is recorded.

4. A method according to claim 1 wherein the measurement of cell permeability is calculated as the volume of fluid crossing the cell membrane per unit area of the cells.

5. A method according to claim 1 wherein the sensor measurements are a record of the passage of cells as a series of voltage pulses, and wherein the amplitude of each pulse is proportional to cell size.

6. A method according to claim 1 wherein sensor measurements are recorded on a cell by cell basis.

7. A method according to claim 1 wherein the recorded sensor measurements are subjected to analysis to calculate cell volume at each of a number of different environmental conditions, said calculation taking into account the shape of cells in the altered cell suspension.

8. A method according to claim 1 wherein fluid is driven across a cell membrane by a lytic agent, thereby causing a change in cell volume.

9. A method according to claim 1 wherein when the sample cell suspension comprises cells with inelastic membranes, environmental parameters are varied such that the cells in the altered sample cell suspension may assume all possible cell shapes and cell volumes.

10. A method according to claim 1 wherein a single environmental parameter, in addition to osmolality, is varied.

11. A method according to claim 10 wherein all other parameters affecting cell volume are held constant.

12. A method according to claim 1 wherein cells in the sample cell suspension or altered sample cell suspension have first cell shapes and cell volumes prior to alteration of one or more environmental parameters and have second cell shapes and cell volumes upon alteration of the one or more environmental parameters, and wherein the cell permeability calculation is determined as cells undergo a change from said first cell shapes and cell volumes to said second cell shapes and cell volumes.

13. A method according to claim 1 wherein Cp rate is determined as a measure of cell permeability, wherein the Cp rate represents a coefficient of permeability which measures the rate of fluid flow across a square meter of membrane in response to a specified pressure.

14. A method according to claim 1 wherein $pK_n$ is determined as a measure of cell permeability, wherein n is a positive integer and $pK_n$ represents a set of permeability measures which describe each pressure where the net permeability rate is zero.

15. A method according to claim 1 wherein $Cp\Delta$ is determined as a measure of cell permeability and wherein $Cp\Delta$ represents the comparison of any two Cp rates and is expressed as the net amount of fluid to cross a cell membrane between any two pressures.

16. A method according to claim 1 wherein $Cp_{max}$ is determined as a measure of cell permeability, wherein $Cp_{max}$ is the maximum flow rate across cell membranes.

17. A method according to claim 1 wherein membrane structural resistance (MRS) is determined as a measure of cell permeability.

18. A method according to claim 1 wherein Cpml is determined as a measure of cell permeability and wherein Cpml is a measure of physiological permeability available to an individual per unit volume of tissue or blood, for a whole organ or total body.

19. A method according to claim 1, performed automatically.

* * * * *